United States Patent [19]

Karalis et al.

[11] Patent Number: 4,864,060

[45] Date of Patent: Sep. 5, 1989

[54] SURFACE ACTIVE COMPOUNDS, METHODS FOR MAKING SAME AND USES THEREOF

[75] Inventors: Anastasios Karalis, Downers Grove; Thomas Morong, Justice; Charles Juszkiewicz, Woodridge, all of Ill.

[73] Assignee: Witco Corporation, New York, N.Y.

[21] Appl. No.: 91,058

[22] Filed: Aug. 31, 1987

[51] Int. Cl.$^4$ ............................................... C07C 91/26
[52] U.S. Cl. ................................... 564/292; 564/294; 564/285; 564/282; 564/291
[58] Field of Search ............... 564/294, 291, 295, 282, 564/285, 292

[56] References Cited

U.S. PATENT DOCUMENTS

| | | | |
|---|---|---|---|
| 3,426,029 | 2/1969 | Beavers et al. | 564/294 |
| 3,466,247 | 9/1969 | Ohtsuka et al. | 564/294 |
| 4,126,562 | 11/1978 | Goffinet et al. | 564/294 |
| 4,138,427 | 2/1979 | Vanlerbergh et al. | 564/294 |
| 4,416,808 | 11/1983 | Blaschke | 564/297 |

FOREIGN PATENT DOCUMENTS 639398  4/1962  Canada ............................... 564/297

*Primary Examiner*—James H. Reamer
*Attorney, Agent, or Firm*—Morton Friedman

[57] ABSTRACT

Aliphatic surface active compounds containing a propylene chain bonded at one end to a cationic quaternary ammonium group and at the other end to an amphoteric amine oxide group, and methods of making and using them.

6 Claims, No Drawings

SURFACE ACTIVE COMPOUNDS, METHODS FOR MAKING SAME AND USES THEREOF

BACKGROUND OF THE INVENTION

FIELD OF THE INVENTION

The present invention relates to new surface active compounds which are also effective textile softening and conditioning agents, hair conditioners, humectants, cationic dispersants and the like.

There are literally tens of thousands of surface active compounds, and if not tens of thousand then, certainly hundreds and indeed thousands of surface active compounds which are used in textile cleaning and laundering operations. Of this latter group, few, if any, are effective to any substantial and practical degree as wash cycle textile softening agents and, of these, none, as far as we are aware, are considered commercially viable.

Most laundry surfactants leave the wash with a very harsh, boardlike feel. On a rating scale of one to ten, with one being very hard and ten being very soft, most surfactants give values of one or two on cotton. A typical 80:20 (tallow-coconut oil) soap gives higher readings with the values being dependent upon concentration and weight ratio of cotton to soap. When clothes are treated in the rinse cycle of an automatic washing machine with a conventional 6% active aqueous quaternary softener, such as dimethyl, dihydrogenated tallow ammonium methosulfate, the softeners' ratings on cotton will usually range from 9 to 10+.

Surfactant materials cover the entire spectrum of charged types of compounds such as:

(1) anionic, as illustrated by fatty acid soaps, sulfonates (e.g. alkyl benzene sulfonates, olefin sulfonates, paraffin sulfonates), sulfates (e.g. sodium lauryl sulfates), ether sulfates (e.g. the sodium salt of the sulfated ethylene oxide condensation with lauryl alcohol);

(2) cationic, such as octadecyl trimethylammonium chloride, cetyl trimethylammonium methyl sulfate, polymeric cationics derived from monomers such as N,N,N-trimethyl-N-methacryloxy (2-hydroxy propyl) ammonium chloride and cationic monomers such as described in U.S. Pat. Nos. 4,212,820 (Hotchkiss et al), 4,098,987 and 4,171,418 (both Baura et al) and 4,426,489 (wessling et al), these patents being merely illustrative and not limitative. The disclosures of the aforementioned United States patents are incorporated herein in their entirety by reference. See also U.S. Pat. Nos. 3,849,426; 3,399,159 (Samorer) and 4,051,158 (Samorer et al). In addition to quaternary ammonium cationic moieties, the compounds with phosphonium, sulfonium, pyridinium and isothiouronium moieties and the like are also among the general and well-known group of cationic surfactants.

(3) Nonionic—These include inter alia, the broad group of the alkylene oxide condensates with a higher molecular weight, reactive H-containing organic hydrophobe, such as an alcohol (e.g. $C_8$ to $C_{30}$ alcohol e.g. stearyl alcohol, 1-octanol, dodecanol, etc.), a polyoxypropylene backbone polymer, a phenol (e.g. nonyl phenol, di-isobutyl phenol), a mercaptan, an amide, an amine, a carboxylic acid, etc. The alkylene oxide should comprise at least a substantial portion of ethylene oxide to provide the usually necessary and required hydrophilic-lipophilic balance (HLB). Other types of nonionics include the tertiary amine oxides such as; dimethyldodecylamine oxide, dimethyltetradecylamine oxide, ethylmethyltetradecylamine oxide, cetyldimethylamine oxide, dimethylstearylamine oxide, cetylethylpropylamine oxide, diethyldodecylamine oxide, diethyltetradecylamine oxide, dipropyldodecylamine oxide, bis-(2-hydroxyethyl) dodecylamine oxide, bis-(2-hydroxypropyl) methyltetradecylamine oxide, diethyloleylamine oxide, dimethyl-2(-hydroxydodecyl) amine oxide and the corresponding decyl, hexadecyl and octadecyl homologs of the above compounds; the phosphine oxides such as: dimethyldodecylphosphine oxide, dimethyltetradecylphosphine oxide, ethylmethyltetradecylphosphine oxide, cetyldimethylphosphine oxide, dimethylstearylphosphine oxide, diethyltetradecylphosphine oxide, dipropyldodecylphosphine oxide, bis-(hydroxymethyl) dodecylphosphine oxide, bis-(2-hydroxyethyl) dodecylphosphine oxide, (2-hydroxypropyl) methyltetradecylphosphine oxide, dimethyloleylphosphine oxide, and dimethyl (2-hydroxydodecyl) phosphine oxide and the corresponding decyl, decadecyl and octadecyl homologs of the above compounds; and sulfoxides of the formula

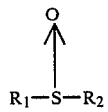

wherein $R_1$ is an alkyl radical containing from about 10 to about 28 carbon atoms, from zero to about five ether linkages and from zero to about two hydroxyl substituents and wherein $R_2$ is an alkyl radical containing from one to three carbon atoms and from zero to two hydroxyl groups, such as:

octadecylmethyl sulfoxide
dodecylmethyl sulfoxide
tetradecylmethyl sulfoxide
3-hydroxytridecyl methyl sulfoxide
3-methoxytridecyl methyl sulfoxide
3-hydroxy-4-dodecoxybutyl methyl sulfoxide
octadecyl 2-hydroxyethyl sulfoxide
dodecylethyl sulfoxide.

(4) Ampholytic—compounds which contain a secondary or tertiary amine group and a long chain (e.g. 8 to 20 carbons), usually aliphatic group containing an anionic water-solubilizing group such as carboxy, sulfate, sulphone, etc. Taurides and isethionates are illustrative of this class.

(5) Zwitterionic—such as 3 (N,N-dimethyl-N-hexadecylammonio)-propane-1-sulfonate and other similar compounds as described in U.S. Pat. Nos. 2,129,264, 2,774,786, 2,813,898, 2,828,332 and 3,529,524. Other types are described in U.S. Pat. Nos. 3,265,719, 2,697,116, 2,669,991 and 2,697,656 and British Patents Nos. 970,883 and 1,046,252.

By far the predominant type of surfactant for laundry cleaning is the anionic type, followed by the nonionic type. Both of these provide excellent detergents for laundering and often they are used in combination to obtain the benefits of each. For example, non-ionics are particularly outstanding on oily soil. It is rare to employ a cationic surfactant with an anionic one due to the "interaction" between the two charged types resulting not only in a neutralization of the charges, but also of the detergency effectiveness. Where the use of small amounts of cationic softeners in combination with anionic surfactants has been successful in yielding a "softergent" (a detergent which also softens the laundry during the wash cycle) this has usually been accomplished by any one or a combination of unique ingredients and processing techniques often with some loss of surfactant and/or softening activity, etc. As an example of the foregoing, attention is directed to the following United States patents:

| U.S. Pat. Nos. | 3,920,563 |
|---|---|
| | 4,082,682 |
| | 4,230,590 |
| | 4,298,480 |
| | 4,329,237 |
| | 4,326,971 |
| | 4,339,335 |
| | 4,446,811 and |
| | 4,450,085. |

Thus, for example, and as shown in U.S. Pat. No. 4,450,085 Wixon), soap, non-ionic surfactant and magnesium sulfate are combined and used as separate and discrete particles in an anionic spray-dried formulation also containing a cationic softener to provide an effective detergent-softener composition. This patent reaffirms the obvious problems pointed out above of using anionic surfactants and cationic compounds (as softeners or otherwise) in combination.

While the use of non-ionic surfactants with cationic compounds does not appear to offer a problem insofar as "charge" interaction is concerned, and such combinations are common in the prior art (see U.S. Pat. Nos. 4,268,401, 4,291,071, 4,233,167 and 4,140,641), there are nevertheless problems here as well. Thus, it is well known that cationic softener effectiveness is often seriously curtailed in the presence of non-ionic surface active materials.

While cationic surfactants as a significant or as a major surfactant component of a laundry detergent is practically non-existent (for many obvious reasons including cost, compatibility, etc.) even were one to be considered, one has to recognize their generally poor foaming characteristics as another contra-indicating factor.

Other problems attendant with the use of the conventional quaternary ammonium compounds as softeners resides in their low water-solubility, the difficulty in forming concentrated and stable aqueous systems, and their difficult handling and processing characteristics as well.

PRIOR ART

In addition to the background art discussion given above, the only additional prior art of which we are aware which is relevant to the present invention is U.S. Pat. No. 4,416,808 issued Nov. 22, 1983. This patent discloses a specific group of bis-betaine-amine oxides of the formula

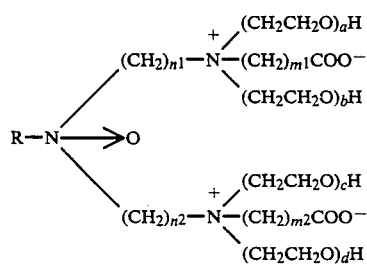

wherein R is a saturated or an olefinically unsaturated hydrocarbon radical having one to three double bonds and eight to 22 carbon atoms, $n^1$ and $n^2$ each is an integer of from 2 to 3, $n^1$ and $n^2$ optionally being identical or different, $m^1$ and $m^2$ is each an integer of from one to four, $m^1$ and $m^2$ optionally being identical or different, and a, b, c and d, being identical or different, each is a number of from one to five, with the proviso that the sum (a+b+c+d) is at most 10.

These compounds are described as particularly useful for skin and hair cleaning due to their mild action and "less pronounced cleansing effect" ..., "thus allowing an increased frequency of their washing or shower bathing." (col. 1, lines 58–62).

SUMMARY OF THE INVENTION

The present invention relates to chemical moieties which in a single molecule provide a quaternary ammonium cationic site and a tertiary amine oxide site so that an effective and outstanding surfactant property along with a softening property is achieved in this single molecular entity. By virtue of the structural relationship of the quaternary nitrogen, the tertiary amine oxide and other hydrophobic and hydrophilic groups, other unique and unexpected characteristics are obtained. Thus it is found that the foaming characteristics are excellent and not affected by the presence of anionics. The products are water soluble and also form stable cationic emulsions with good cosmetic esthetics. It has further been found that the compounds exhibit strong substantivity to glass, metal, fabrics, skin and hair.

The products of this invention are in general prepared by the alkoxylation of an aliphatic diamine containing a primary amino and a secondary amino nitrogen to produce two tertiary amine groups. One is quaternized and the other converted to a tertiary amino oxide group.

DETAILED DESCRIPTION OF THE INVENTION

The compounds of this invention are selected from those of the following general formulas:

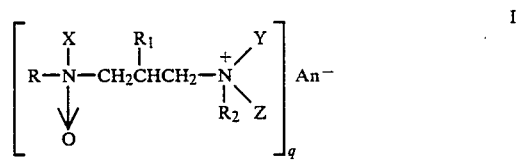

wherein
(a) R is an aliphatic radical, preferably alkyl (straight chain with little or no branching) or unsaturated (preferably monounsaturated) alkyl of $C_6$ to $C_{30}$ and, more preferably, $C_8$ to $C_{20}$ and, most preferably, $C_{10}$ to $C_{18}$;
(b) $R_1$ is hydrogen or $C_1$ to $C_6$ alkyl, or $C_2$ to $C_6$ unsaturated (preferably monounsaturated) alkyl, e.g. alkenyl;
(c) $R_2$ is the organic residue of the alkylating agent e.g. $C_1$ to $C_{18}$ alkyl (from alkyl halide, sulfate, etc.), $C_2$ to $C_{18}$ unsaturated alkyl or benzyl or phenethyl, etc.; preferred groups are methyl, ethyl and benzyl;
(d) X, Y and Z are independently selected from lower alkyl (e.g. $C_1$ to $C_6$), unsaturated lower alkyl (e.g. $C_2$ to $C_6$), preferably mono-unsaturated alkyl, such as isopropenyl, etc., and more preferably hydroxyalkyl, hydroxyalkoxyalkyl or hydroxypolyalkoxy alkyl of the formula —

$$(CH_2\underset{R_3}{CHO}-)_nH$$

wherein $R_3$ is independently selected from hydrogen and $C_1$ to $C_4$ alkyl and n is independently an integer from 1 to 20.

(e) An is a counterion, such as chloride, bromide, methosulfate, ethosulfate, phosphate, acetate or any other suitable water-solubilizing anion derived from the alkylating (quaternizing) agent;

(f) q is an integer of 1 to 4 and equal to the valence of An; and (g) at least one of X, Y and Z, preferably two and, more preferably, each of X, Y and Z is $$(-CH_2-\underset{R_3}{CH}-O)_nH,$$

and $$\left[ R-\underset{\underset{R_2}{|}}{\overset{\overset{X}{|}}{\underset{+}{N}}}-CH_2CHCH_2-N\underset{\underset{O}{\Downarrow}}{\overset{\overset{R_1}{|}}{\diagdown}}\overset{Y}{\diagup}_{Z} \right]_q An^-$$
II wherein R, $R_1$, $R_2$, X, Y, Z, q and An are selected similarly as above set forth for formula I, and mixtures of I and II.

Preferred compounds within the general formulas I and II are those in which X, Y, and Z are each $(CH_2-CHR_3-O)_nH$, $R_1$ is hydrogen and $R_3$ is preferably methyl.

For illustrative purposes only, specific compounds include the following:

Formula I compounds:

(1) R is oleyl, X, Y and Z are each $CH_2CH_2OH$, $R_1$ is $C_2H_5$, $R_2$ is $CH_3$, and An is Cl.

(2) R is tallow alkyl, X, Y and Z are each $CH_2CH_2OH$, $R_1$ is butenyl, $R_2$ is benzyl, and An is Cl.

(3) R is tallow alkyl, X, Y and Z are each $$\underset{CH_2CHOH,}{\overset{CH_2CH_3}{|}}$$

$R_1$ is H, $R_2$ is $CH_2CH_3$, and An is Br.

(4) R is tallow alkyl, X, Y and Z are each $$\underset{CH_2CHOH,}{\overset{CH_3}{|}}$$

$R_1$ is H, $R_2$ is $CH_3$, and An is Cl.

(5) R is $C_{14}H_{29}$, X, Y and Z are each $$\underset{CH_2CHOCH_2CH_2OH,}{\overset{CH_3}{|}}$$

$R_1$ is H, $R_2$ is $CH_3$, and An is methyl sulfate.

Formula II compounds:

(6)–(10) corresponding to (1)–(5) but in which the left hand N is quaternized (bonded to $R_2$) and the right hand N is oxidized (bonded to O).

In the above formulae, the tallow alkyl (from tallow amine precursor) is typically a mixture of natural saturated and unsaturated $C_{12}$ to $C_{20}$ aliphatic hydrocarbons, the chain distribution being generally:

| | |
|---|---|
| $C_{18}$ saturated | 16–22% |
| $C_{18}$ unsaturated | 40–50% |
| $C_{16}$ | 25–30% |
| $C_{12}$–$C_{14}$ and $C_{20}$ | 2–7% |

A typical tallow alkyl might contain 29% palmityl, 21% stearyl, 41% oleyl, 2% linoleyl, 3% myristyl, and the balance $C_{12}$ and $C_{20}$ alkyls.

The general method for preparing the compounds of this invention involves the following basic reactions:

(a) Reaction of a primary amine with acylonitrile, or methacrylonitrile (or other reactive nitrile) to form a cyanoalkyl substituted amine (i.e. secondary amine);

(b) Reduction of the nitrile group to primary amine;

(c) Reaction of resulting diamine with alkylene oxide (at least one mole, preferably two, more preferably, three to four or even more moles per mole of diamine) to ensure the conversion of both the primary amine group and the secondary amine group to alkoxylated tertiary amine groups;

(d) Reaction of the alkoxylated tertiary amine from (c) with an equivalent weight of alkylating agent to quaternize one of the tertiary amino group;

(e) Oxidation of the tertiary (unquaternized) amino group to a tertiary amine oxide.

Where the reaction (c) is conducted with less than sufficient alkylene oxide to convert both nitrogens to tertiary form, in reaction (d) the equivalent weight of alkylating (i.e. quaternizing) agent is doubled or tripled to introduce two or three alkyl moieties, but always leaving one nitrogen in tertiary form for oxidation to the amine oxide. In the preferred embodiments of the invention as pointed out above, each of the hydrogens of the original primary nitrogen is substituted with an hydroxyalkyl, hydroxyalkoxyalkyl or hydroxypolyalkoxyalkyl as is the single hydrogen of the secondary amine group.

Reactions (a) and (b) and their varying conditions of catalyst, solvent, pressure, temperature, etc. are known in the art. The diamines thus produced are often available commercially. Thus a suitable product is Kemamine D 974, a tallow diamine available from Humko Chemical Company. See also U.S. Pat. No. 3,660,460 for illustrative reaction (a) conditions and procedures for preparing monocyanoethylated amines, which, when reduced, form diamines. This entire patent is incorporated herein by reference. The reduction of the cyanoethylated amine to the diamine (reaction (b)) involves use of a conventional (e.g. Raney nickel, Raney cobalt, etc.) hydrogenation catalyst under pressure (e.g. 50 to 200 bar of hydrogen) and at temperatures usually from 50 to 200 degrees C. for periods of time, of from about 30 minutes to five or six hours.

The oxyalkylation reaction (c) employs, generally, a $C_1$ to $C_6$ alkylene oxide or vicinal epoxide such as ethylene oxide, propylene oxide, butylene oxide, etc., usually under pressure (e.g. 1 to 5 bar) and usually and preferably at an elevated temperature (e.g. 60 degrees C. to 200 degrees C., preferably 75 degrees C. to 120 degrees C., and, more preferably, 85 degrees C. to 99 degrees C.). In the preferred embodiments of this reaction, at least three, and preferably up to four moles of oxyalkylating agent are used per mole of diamine. This results in the desired bis tertiary amine formation, i.e. each of the three reactive hydrogens on the two nitrogen atoms is initially substituted by an hydroxyalkyl group.

When more than three moles of oxyalkylating reagent per mole of diamine are used, the oxyalkyl chains may, under suitable conditions, propagate by reaction of the terminal hydroxyl with the additional oxyalkylating reagent. Since each of the initial three hydroxyalkyl groups are of the same order of reactivity, the products tend to be a mixture. Thus, for example, reacting four moles of propylene oxide with a stearyl diamine ($C_{18}H_{37}NHCH_2CH_2CH_2NH_2$) one could expect some of each of the following, in addition to the initial product containing three N substituted hydroxypropyl groups:

$$C_{18}H_{37}N(CH_2CHO)_2H / CH_3)-CH_2CH_2CH_2-N(CH_2CHOH/CH_3)(CH_2CHOH/CH_3) \quad (1)$$

$$C_{18}H_{37}N(CH_2CHOH/CH_3)-CH_2CH_2CH_2-N((CH_2CHO)_2H/CH_3)(CH_2CH-OH/CH_3) \quad (2)$$

With five moles of propylene oxide, the permutations obviously increase and, with six moles, at least some of the product would have the formula $$C_{18}H_{37}N((CH_2CHO)_2H/CH_3)-CH_2CH_2CH_2-N((CH_2CHO)_2H/CH_3)((CH_2CHO)_2H/CH_3) \quad (3)$$

mixed with the other variants.

In the oxyalkylating reaction, one may employ the conventional catalysts, e.g. caustic solution, but none is necessary except at high levels of oxyalkylating reagent. In general, it is convenient to refer to the reaction products of the epoxide and the diamine as products having the molecular configuration of the products produced by the reaction of the specified types of diamines with the named epoxides, also setting out the mole ratios of the two as well.

The quaternizing reaction (d) is done in the usual manner employing about equal moles of the alkylating agent and the alkoxylated di-tertiarty amines from (c). Temperatures and pressures would be generally similar to those used in the alkoxylation step (c).

The oxidation step (e) is carried out in a conventional manner using aqueous hydrogen peroxide (or other equivalent peroxides such as sodium perborate mono or tetrahydrate, urea peroxide, organic peracids etc.) usually of 20 to 50% concentration, preferably 30% strength. Convenient temperatures are 40 degrees C. to about 60 degrees C., with around 55 degrees C. being preferred.

A slight excess of the peroxide over the stoichiometric amount may be desirable, e.g. up to about 3% excess.

The following examples will serve to illustrate the present invention without being deemed limitative thereof. All amounts and proportions referred to herein and in the appended claims are by weight and temperatures are in degrees F., unless otherwise indicated.

EXAMPLE 1

(A) Oxyalkylation

To 1871 parts (about 6 moles) of a tallow diamine (Kemamine D974) of the following formula:

tallow—$NHCH_2CH_2CH_2$—$NH_2$ in an autoclave equipped with a stirrer and cooling coils, there is added 19 parts of water and the mixture is heated to 195 degrees F. (90.50 degrees C.). To this is then added 1150 (about 20 moles) parts of propylene oxide over a period of two hours at a pressure of 30 psig. When the addition is complete, heating is continued for an additional four hours at this temperature. The resultant product is then stripped of unreacted propylene oxide and cooled. The yield is 3005 parts.

(B) Quaternization

To 1442 parts of the above product, there is added 142 parts of methyl alcohol and 14 parts of water. This is heated to 195 degrees F. (90.50 degrees C. ) in an autoclave and 124 parts of methyl chloride is added over a period of six hours at a pressur of 45 psig. This material is diluted with 100 parts of water and cooled to 125 degrees F. (51.50 degrees C.).

(C) Oxidation 126 parts of 30% aqueous hydrogen peroxide is then added over a period of one hour and heating is continued for four more hours at this temperature (100 degrees to 125 degrees F.). The product is then stripped under vacuum for a period of one hour, and has Formula I (4) and/or II (4) above wherein R is tallow alkyl; X, Y and Z are each hydroxypropyl; $R_1$ is hydrogen; $R_2$ is methyl; An is chloride and q is 1.

EXAMPLE 2

Example 1 is repeated using equivalent amounts of the following diamines in place of the diamine of Example 1:

$$\begin{array}{ll} C_{16}H_{33}N(H)-CH_2CH_2CH_2NH_2 & (a) \\ C_{14}H_{29}N(H)-CH_2CH_2CH_2NH_2 & (b) \\ C_{12}H_{25}N(H)-CH_2CH_2CH_2NH_2 & (c) \\ C_{10}H_{21}N(H)-CH_2CH_2CH_2NH_2 & (d) \\ C_8H_{17}N(H)-CH_2CH_2CH_2NH_2 & (e) \\ C_{20}H_{41}N(H)-CH_2CH_2CH_2NH_2 & (f) \end{array}$$

-continued

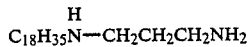   (g)

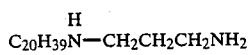   (h)

Similar Formula I and/or Formula II products are obtained

EXAMPLE 3

Examples 1 and 2 are repeated using in place of 20 molar parts (i.e. 1150 parts) of propylene oxide, 40 molar parts of propylene oxide. The major product in each instance contains a hydroxypropoxypropyl group for each of the three reactive hydrogens on the amino groups.

EXAMPLE 4

Example 3 is repeated using in place of the 40 molar parts of propylene oxide of example 3:

(a) 20 molar parts propylene oxide and, after stripping unreacted propylene oxide, further adding 20 molar parts ethylene oxide (the major product in each instance contains a hydroxyethoxypropyl group for each of the three reactive hydrogens.)

(b) 10 molar parts propylene oxide and 248 parts methyl chloride instead of 124 parts methyl chloride (the major product in each instance contains on average about half the said reactive hydrogens replaced by hydroxypropyl and about half by methyl.

EXAMPLE 5

Each of the foregoing examples is repeated utilizing in place of the alkylene oxides used therein the following:

butylene oxide    (a)

   (b)

   (c)

   (d)

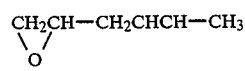   (e)

Formula I and/or II products are obtained in which the X, Y and Z groups are derived from the respective (a) to (e) oxides.

The compounds of this invention have a multiplicity of uses and among them their use as, and in, laundry and other detergent compositions is of major importance. In laundry detergents, the compounds demonstrate excellent cleaning performance and also impart softness to the laundry. The compounds may be used with other surfactants and with the usual builders, and other adjuvants at any stage in the preparation of the detergent compositions.

The detergent compositions preferably include water soluble alkaline to neutral builder salt in amounts of from about 10 to 60% by weight of total composition. Useful herein are the organic and inorganic builders including the alkali metal and alkaline earth metal phosphates, particularly the condensed phosphates, such as the pyrophosphates or tripolyphosphate, silicates, borates, carbonates, bicarbonates and the like. Species thereof include sodium tripolyphosphate, trisodium phosphate, tetrasodium pyrophosphate, sodium acid pyrophosphate, sodium monobasic phosphate, sodium dibasic phosphate, sodium hexametaphosphate, alkali metal silicates, such as sodium metasilicate, sodium silicates: ($SiO_2/Na_2O$ of 1.6:1 to 3.2:1), sodium carbonate, sodium sulfate, borax (sodium tetraborate), ethylene diamine tetraacetic acid tetrasodium salt, trisodium nitrilotri-acetate and the like and mixtures of the foregoing. Builder salt may be selected so as to provide either phosphate-containing or phosphate-free detergents. As to the latter embodiments, sodium carbonate is particularly effective. Another material found to provide good detergency effects is metakaolin which is generally produced by heating kaolinite lattice to drive off water producing a material which is substantially amorphous by x-ray examination but which retains some of the structural order of the kaolinite. Discussions of kaolin and metakaolin are found in U.S. Pat. No. 4,075,280, columns 3 and 4, and Grimshaw, "The Chemistry And Physics of Clays and Allied Ceramic Materials," (4th ed. Wiley-Interscience), pages 723–727). The metakaolin also appears to have softening utility. As to the latter, the most effective metakaolins appear to be those which behave best in the reaction with sodium hydroxide to form zeolite 4A as described in U.S. Pat. No. 3,114,603, which refers to such materials as "reactive kaolin". As explained in the referenced sources, metakaolin is an aluminosilicate. The metakaolin and/or a zeolite is included in about the same amounts as the builder salt, and preferably supplmental thereto, e.g. zeolite-silicate in a ratio of 6:1. A particularly useful form of the metakaolin is that available commercially as Satintone No. 2.

Preferred optional ingredients useful in detergents include perfume such as Genie perfume; optical brighteners and bluing agents which may be dyes or pigments, suitable materials in this regard including stilbene and Tinopal 5BM brighteners and particularly in combination and Direct Brilliant Sky Blue 6B, Solophenyl Violet 4BL, Cibacete, Brilliant Blue RBL and Cibacete Violet B, Polar Brilliant Blue RAW and Calcocid Blue 2G bluing agents. The brightener may be included in amounts ranging up to about 1% of the total composition while bluing agents may range up to about 0.1% preferably up to about 0.01% of total composition. Bluing agent, e.g., Polar Brilliant Blue may be included in the soap spaghetti. In either case, the amount need only be minimal to be effective.

Other optional ingredients in the detergents include bleaching agents which may be of the oxygen or chlorine liberating type; Oxygen type bleaching agents include sodium and potassium perborate, potassium monopersulfate and the like, while chlorine bleaches are typified by sodium hypochlorite, potassium dichloroisocyanurate, trichloroisocyanuric acid and the like. The latter chlorine-liberating bleaches are representative of the broad class of water soluble, organic, dry solid bleaches known as the N-chloroimides including their alkali metal salts. These cyclic imides have from about 4 to 6 members in the ring and are described in detail in U.S. Pat. No. 3,325,414. They are generally used in proportions ranging from about 0.1 to 25% by weight of total solids or from about 0.05% to about 20% based on total detergent composition.

Yet additional optional ingredients in detergents include water soluble and/or dispersible hydrophobic colloidal cellulosic soil suspending agents. Methyl cellulose, e.g. Methocel, is particularly effective and especially in the washing of cotton and synthetic fibers such as nylon, dacron and resin treated cotton. The additional soil suspending agent may be included in amounts up to about 4% based on total detergent composition. However, it must be emphasized that the nonionic organic surfactant component of the soap spaghetti supplies at least a major part of the anti-redeposition or soil suspending function, its effectiveness in this regard being significantly augmented by the soap material as previously explained.

Fillers may also be included in addition to the aforementioned ingredients, such as sodium sulfate, sodium chloride and the like. The amount may range from about 5% up to about 40% of total composition.

The detergent compositions may be prepared by conventional processing such as spray drying a crutcher mix of surfactant, builder, filler, etc. without volatile ingredients such as perfume or ingredients otherwise adversely affected by the spray drying process, such as peroxygen bleach, e.g. sodium perborate. Ingredients of this type are preferably post blended. A typical procedure would be as follows: Water is added to a crutcher followed in order by anionic surfactant, sodium silicate, optional ingredients where used such as Satintone #2 and filler such as sodium sulfate and builder salt. The crutcher mixture is heated to about 140 degrees F. before addition of builder, e.g. sodium tripoly-phosphate and the solids content of the crutched mixture before spray drying is about 55–65%. Spray drying may be carried out in a conventional manner by pumping the hot mixture from the crutcher to a spray tower where the mixture passes through a spray nozzle into a hot evaporative atmosphere. Bleach and other materials remaining to be added are incorporated into the cooled, dried detergent mass by any suitable means, such as simple mechanical mixing. The compounds of this invention may be added with the bleach or at an earlier stage in the preparation.

Other uses of the compounds of this invention include formulating into hair cleaning and conditioning preparations, skin treatment and conditioners, and others.

Some illustrations of a car wash formulation and hair conditioning shampoo are as follows:

EXAMPLE 6

| Car Wash formulation: | |
|---|---|
| Product of Example 1 | 2% |
| Water | 98% |

The product foams well, sponges on the car well, has very good water rinse off properties, and leaves a water-resistant film, which dries to a shine.

EXAMPLE 7

| Hair Shampoo: | |
|---|---|
| Product of Example 1 | 12% |
| Natrosol 250HR | 1% |
| (hydroxyethylcellulose of Hercules) | |
| Water | 87% |

The Natrosol is first dissolved in 50 to 50 degrees C. water and then the product of Example 1 is added. Finally, perfumes, some preservative and suitable color are added.

The product lathers with a luxurious foam and, on rinsing the hair, is very manageable indicating substantivity and conditioning properties vis-a-vis the hair.

EXAMPLE 8

A detergent composition suitable for laundering clothes is prepared having the following ingredients:

| | Weight % |
|---|---|
| Product of Example 1 | 15.0 |
| Sodium tripolyphosphate (hexahydrate) | 25.0 |
| Sodium silicate (NAO:SiO$_2$ ratio of 1:2.5) | 10.0 |
| Carboxymethylcellulose | 2.0 |
| Proteolytic Enzyme | 1.0 |
| Brightener (Tropal 3BM) | 2.0 |
| Neodol 23-6.5/Shell | 5.0 |
| Sodium carbonate | 10.0 |
| Sodium Sulfate, water, perfume, color, balance to | 100.0% |

EXAMPLE 9

Example 8 is repeated replacing half of the tripolyphosphate with Zeolite 4A, crystalline (particle size 4 to 8 microns).

Although in the above-described method of preparing the compounds of this invention oxidation reaction (e) follows quaternization reaction (d), it will be understood that the method in which reaction (d) follows reaction (e) is to be regarded as equivalent, substantially similar products being obtainable thereby.

This invention has been disclosed with respect to preferred embodiments andd it will be understood that modifications and variations obvious to those skilled in the art are to be included within the spirit and purview of this application and the scope of the appended claims.

We claim:

1. A compound selected from those of the following formulae:

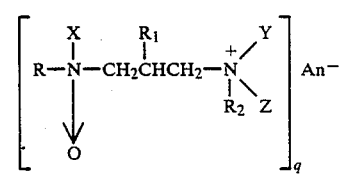

and

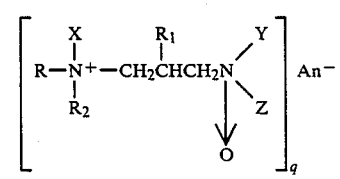

and mixtures of I and II,
wherein (1) R is a $C_6$ to $C_{30}$ aliphatic radical, preferably alkyl or alkenyl;
(2) X, Y and Z are independently selected from the group consisting of $C_1$ to $C_6$ alkyl, $C_2$ to $C_6$ alkenyl and $(-CH_2CHR_3O-)_nH$ groups wherein $R_3$ is independently selected from hydrogen and $C_1$ to $C_4$ alkyl, and n is independently an integer from 1 to 20;
(3) $R_2$ is $C_1$ to $C_{18}$ alkyl, $C_2$ to $C_{18}$ alkenyl, benzyl or phenylethyl;
(4) $R_1$ is hydrogen, $C_1$ to $C_4$ alkyl or $C_2$ to $C_6$ alkenyl;
(5) An is a water-solubilizing anion;
(6) q is an integer of 1 to 4 equivalent to the valence of the anion (An); and at least one of X, Y and Z is a $(-CH_2CHR_3O-)_nH$ group.

2. A compound as defined in claim 1, wherein X, Y and Z are each $(-CH_2CHR_3O-)_nH$ and $R_1$ is hydrogen.

3. A compound as defined in claim 2, wherein n in each of X, Y and Z is 1.

4. A compound as defined in claim 3 wherein X, Y and Z are each hydroxypropyl.

5. A compound as defined in claim 4 wherein R is tallow alkyl.

6. A compound as defined in claim 5 wherein $R_2$ is methyl, q is one, and An is chloride.

* * * * *